(12) United States Patent
Brasshears et al.

(10) Patent No.: US 10,420,806 B2
(45) Date of Patent: Sep. 24, 2019

(54) LACTIC ACID AND OTHER PROBIOTIC BACTERIA TO REDUCE PATHOGENS IN LYMPH NODES AND OTHER LYMPHATIC TISSUES OF LIVESTOCK ANIMALS

(71) Applicant: Texas Tech University System, Lubbock, TX (US)

(72) Inventors: Mindy M. Brasshears, Wolfforth, TX (US); Guy H. Loneragan, Lubbock, TX (US); Kendra Nightingale, Lubbock, TX (US); J. Chance Brooks, Wolfforth, TX (US)

(73) Assignee: Texas Tech University System, Lubbock, TX (US)

( * ) Notice: Subject to any disclaimer, the term of this patent is extended or adjusted under 35 U.S.C. 154(b) by 1035 days.

(21) Appl. No.: 14/585,850

(22) Filed: Dec. 30, 2014

(65) Prior Publication Data

US 2015/0182565 A1 Jul. 2, 2015

Related U.S. Application Data

(60) Provisional application No. 61/921,890, filed on Dec. 30, 2013.

(51) Int. Cl.
*A61K 35/747* (2015.01)
*A61K 35/741* (2015.01)
*C12Q 1/18* (2006.01)
*A61K 35/00* (2006.01)

(52) U.S. Cl.
CPC .......... *A61K 35/747* (2013.01); *A61K 35/741* (2013.01); *C12Q 1/18* (2013.01); *A61K 2035/115* (2013.01)

(58) Field of Classification Search
CPC .................................................. A61K 35/747
See application file for complete search history.

(56) References Cited

U.S. PATENT DOCUMENTS

| 7,063,836 | B2 | 6/2006 | Garner et al. |
| 2004/0115177 | A1 | 6/2004 | Harris et al. |
| 2010/0047209 | A1 | 2/2010 | Stanton et al. |
| 2011/0256116 | A1 | 10/2011 | Ware et al. |

OTHER PUBLICATIONS

Arthur et al (J. Food Protect., 71(8):1685-1688 (2008) (Year: 2008).*
Gragg, Sara E. et al., "Substantial within-Animal Diversity of *Salmonella* Isolates form Lymph Nodes, Feces, and Hides of Cattle at Slaughter," Applied and Environmental Microbiology, Aug. 2013 vol. 79 No. 15 p. 4744-4750.

* cited by examiner

*Primary Examiner* — Thomas J. Visone
(74) *Attorney, Agent, or Firm* — Edwin S. Flores; Daniel J. Chalker; Chalker Flores, LLP

(57) ABSTRACT

The present invention includes compositions and methods for eliminating or reducing microbial contamination in lymph nodes that enter the food supply from livestock comprising: identifying an animal in need of eliminating or reducing microbial contamination in non-gut associated lymph nodes that enter the food supply, and providing the animal with an effective amount of a lactic acid bacteria or probiotic bacterial sufficient to reduce or eliminate the microbial contamination in non-gut associated lymph nodes.

17 Claims, 2 Drawing Sheets

LACTIC ACID AND OTHER PROBIOTIC BACTERIA TO REDUCE PATHOGENS IN LYMPH NODES AND OTHER LYMPHATIC TISSUES OF LIVESTOCK ANIMALS

CROSS-REFERENCE TO RELATED APPLICATIONS

This application claims priority to U.S. Provisional Application Ser. No. 61/921,890, filed Dec. 30, 2013, the entire contents of which are incorporated herein by reference.

TECHNICAL FIELD OF THE INVENTION

The present invention relates in general to the field of bacterial contamination of foodstuffs, and more particularly, to the use of lactic acid and other probiotic bacteria to reduce pathogens in lymph nodes and other non-mesenteric lymphatic tissues of livestock animals.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with bacterial contamination of livestock.

United States Patent Application Publication No. 20040115177, filed by Harris, et al., entitled "Probiotic compositions and methods against bacterial infection in livestock animals", is directed to methods of administering probiotic bacteria to livestock animals in an amount effective to reduce the amount of hazardous bacteria found in gut-associated lymph nodes. Probiotic bacteria in an acceptable carrier are administered to the livestock at a selected time before transportation of the animal for harvest or other purposes. The invention also provides compositions comprising probiotic bacteria in an amount effective to reduce the amount of *Salmonella* in livestock animals, e.g., in their feces.

United States Patent Application Publication No. 20100047209, filed by Stanton, et al., entitled "Probiotic composition suitable for animals", is directed to a probiotic composition to alleviate *Salmonella* infection in farm animals. The composition may comprise at least one of *Lactobacillus murinus, Lactobacillus pentosus, Lactobacillus salivarius* sub-species *salivarius*, and *Pediococcus pentosaceus*. The composition may be formulated as an animal feedstuff, or as a pharmaceutical composition.

United States Patent Application Publication No. 20110256116, filed by Ware, et al., entitled "Low/High Dose Probiotic Supplements And Methods Of Their Use", is directed to methods and compositions are hereby disclosed for reducing the numbers of *E. coli* O157:H7, *Salmonella* or other pathogens in an animal. The methods include administering to the animal a lactic acid producing bacterium at a relatively low dosage in combination with a lactate utilizing bacterium, followed by administration of the lactic acid producing bacterium at a relatively high dosage. The methods disclosed help achieve pre-harvest food safety and enhance feed performance while keeping the total cost relatively low. The preferred lactic acid producing bacterium is *Lactobacillus acidophilus/animalis* and the preferred lactate utilizing bacterium is *Propionibacterium freudenreichii*.

U.S. Pat. No. 7,063,836, issued to Garner, et al., entitled, "Compositions and methods for inhibiting pathogenic growth," is directed to methods and compositions for treating an animal to inhibit the incidence and growth of *E. coli* O157:H7 and other pathogenic bacteria. The method of treatment includes administering a therapeutically effective amount of *Lactobacillus acidophilus* or one or a combination of a number of other probiotic bacteria to an animal. An alternative treatment method comprises administering a therapeutically effective amount of a lactic acid producing bacterium such as *Lactobacillus acidophilus* in combination with a lactate utilizing bacterium such as *Propionibacterium freudenreichii*.

SUMMARY OF THE INVENTION

The present invention provides compositions and methods for reducing the amount of bacteria found in lymph nodes that enter the food chain. Specifically, the present invention is directed to lactic acid bacteria and other probiotic bacteria used in feed, e.g., as a food additive, to reduce or eliminate the amount of microbes, e.g., bacteria, which enter food via non-gut associated lymph nodes.

In one embodiment, the present invention includes a method of eliminating or reducing microbial contamination in lymph nodes that enter the food supply from livestock comprising: identifying an animal in need of eliminating or reducing microbial contamination in non-gut associated lymph nodes that enter the food supply; and providing the animal with an effective amount of a lactic acid bacteria or probiotic bacterial sufficient to reduce or eliminate the microbial contamination in non-gut associated lymph nodes. In one aspect, the lymph nodes are selected from at least one of popliteal, intercostal, suprasternal, presternal, prepectoral, precrural, prescapular, ischiadic, prefemoral, sacral, sternal, cervical, renal, superficial inguinal, internal iliac, and external iliac, submaxillary, parotid, retropharyngeal, and lumbar lymph nodes. In another aspect, the lactic acid bacteria is Lactobacilli NP51. In another aspect, the probiotic bacteria is *Propionibacterium* PF24. In another aspect, the lactic acid bacteria is Lactobacilli, NP51, and is combined with the probiotic bacteria *Propionibacterium*, PF24. In another aspect, the lymph nodes inadvertently enter the food supply. In another aspect, the lymph nodes are non-mesenteric. In another aspect, the animal is selected from cattle, pigs, sheep, goats, bison, rabbit, turkey, goose, duck, or chicken.

In another embodiment, the present invention includes a composition for eliminating or reducing microbial contamination in lymph nodes that enter the food supply from livestock comprising an effective amount or a lactic acid bacteria or probiotic bacterial sufficient to reduce or eliminate the microbial contamination in non-gut associated lymph nodes. In one aspect, the lymph nodes are selected from at least one of popliteal, intercostal, suprasternal, presternal, prepectoral, precrural, prescapular, ischiadic, prefemoral, sacral, sternal, cervical, renal, superficial inguinal, internal iliac, and external iliac, submaxillary, parotid, retropharyngeal, and lumbar lymph nodes. In another aspect, the lactic acid bacteria is Lactobacilli NP51. In another aspect, the probiotic bacteria is *Propionibacterium* PF24. In another aspect, the lactic acid bacteria is Lactobacilli NP51, and is combined with the probiotic bacteria *Propionibacterium* PF24. In another aspect, the lymph nodes inadvertently enter the food supply. In another aspect, the lymph nodes are non-mesenteric. In another aspect, the animal is selected from cattle, pigs, sheep, goats, bison, rabbit, turkey, goose, duck, or chicken. In another aspect, the microbes that infect the non-gut-associated lymph nodes are selected from at least one of bacteria and viruses which are both food-borne human and animal pathogens. In another aspect, the microbes that infect the non-gut-associated lymph nodes are selected from at least one of *Salmonella*, pathogenic *E. coli, Campylobacter*, or *Listeria monocytogenes*.

In yet another embodiment, the present invention includes a food additive comprising a Lactobacilli NP51 in combination with *Propionibacterium* PF24 in an amount sufficient to reduce or eliminate the microbial contamination in non-gut associated lymph nodes.

In one embodiment, the present invention includes a method of identifying a candidate probiotic believed to be useful in eliminating or reducing microbial contamination in lymph nodes that enter the food supply from livestock, the method comprising: a) measuring the amount of bacteria from non-gut associated lymph nodes from a set of animals; b) administering a candidate probiotic to a first subset of the animals, and a placebo to a second subset of the animals; c) repeating step a) after the administration of the candidate probiotic or the placebo; and d) determining if the candidate probiotic reduces or eliminates the amount of bacteria from non-gut associated lymph nodes, that is statistically significant as compared to any reduction occurring in the second subset of animals, wherein a statistically significant reduction indicates that the candidate probiotic is useful in reducing or eliminating the amount of bacteria from non-gut associated lymph nodes. In one aspect, the lymph nodes are selected from at least one of popliteal, intercostal, suprasternal, presternal, prepectoral, precrural, prescapular, ischiadic, prefemoral, sacral, sternal, cervical, renal, superficial inguinal, internal iliac, and external iliac, submaxillary, parotid, retropharyngeal, and lumbar lymph nodes. In another aspect, the lymph nodes inadvertently enter the food supply. In another aspect, the lymph nodes are non-mesenteric. In another aspect, the animal is selected from cattle, pigs, sheep, goats, bison, rabbit, turkey, goose, duck, or chicken. In another aspect, the microbes that infect the non-gut-associated lymph nodes are selected from at least one of bacteria and viruses that are both food-borne human and animal pathogens. In another aspect, the microbes that infect the non-gut-associated lymph nodes are selected from at least one of *Salmonella*, pathogenic *E. coli, Campylobacter*, or *Listeria monocytogenes*.

In yet another embodiment, the present invention includes a method of eliminating or reducing bacterial contamination in lymph nodes that enter the food supply from livestock comprising: identifying an animal in need of eliminating or reducing bacterial contamination in non-gut associated lymph nodes that enter the food supply; and providing the animal with an effective amount or a lactic acid bacteria or probiotic bacterial sufficient to reduce or eliminate the bacterial contamination in non-gut associated lymph nodes. In one aspect, the lymph nodes are selected from at least one of popliteal, intercostal, suprasternal, presternal, prepectoral, precrural, prescapular, ischiadic, prefemoral, sacral, sternal, cervical, renal, superficial inguinal, internal iliac, and external iliac, submaxillary, parotid, retropharyngeal, and lumbar lymph nodes. In another aspect, the lactic acid bacteria is Lactobacilli NP51. In another aspect, the probiotic bacteria is *Propionibacterium* PF24. In another aspect, the lactic acid bacteria is Lactobacilli, NP51, and is combined with the probiotic bacteria *Propionibacterium*, PF24. In another aspect, the lymph nodes inadvertently enter the food supply. In another aspect, the lymph nodes are non-mesenteric. In another aspect, the animal is selected from cattle, pigs, sheep, goats, bison, rabbit, turkey, goose, duck, or chicken. In another aspect, the bacteria that infect the non-gut-associated lymph nodes are selected from at least one of *Salmonella*, pathogenic *E. coli, Campylobacter*, or *Listeria monocytogenes*.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
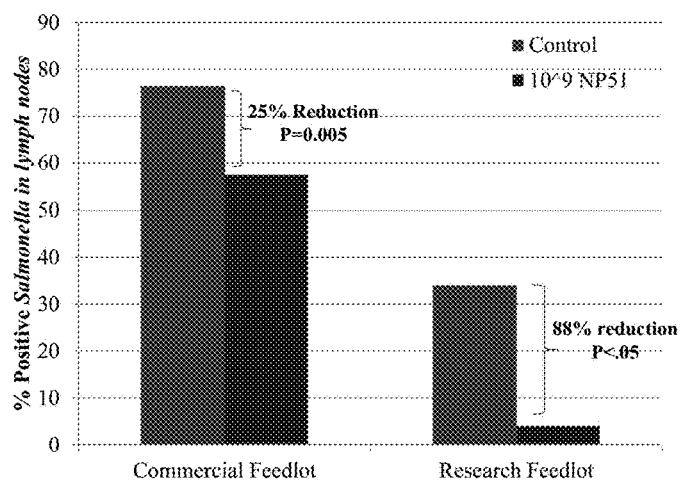
FIGS. 1A and 1B show the *Salmonella* prevalence in lymph nodes (FIG. 1A) and *Escherichia coli* O157 prevalence in fecal samples (FIG. 1B) of cattle fed HNP51 ($10^9$/head/day) at a commercial and research feedlot.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "subject," "patient" and "individual" are used interchangeably herein, to refer to a mammal (e.g., livestock, such as, cattle, pigs, sheep, goats, bison, rabbit, turkey, goose, duck, or chicken) to be treated using the present invention.

As used herein, the terms "effective amount" and "safe and effective amount" refer to the quantity of the lactic acid bacteria or probiotic bacterial of the present invention that is sufficient to yield a desired therapeutic response without undue adverse side effects within a reasonable benefit/risk ratio. Non-limiting examples of adverse effects include immune reactions, viral, bacterial or fungal infections, weigh-loss, or intestinal disorders.

As used herein, the term "therapeutically effective amount" means an amount of a composition as described herein effective to yield the desired therapeutic response.

The specific effective amount or therapeutically effective amount will vary with such factors as the particular condition being treated, the physical condition of the patient, the type of mammal or animal being treated, the duration of the treatment, the nature of concurrent therapy (if any), and the specific formulations employed and the lactic acid bacteria or probiotic bacterial of the present invention.

As used herein, the term "treatment" refers to the application or administration of the lactic acid bacteria or probiotic bacterial to a subject, or application or administration of the therapeutic agent to a subject that may develop a disease or infection or has a disease, symptom or predisposition to a disease. The treatment is provided to the subject to prevent, cure, heal, alleviate, relieve, alter, remedy, ameliorate, improve or affect the disease, the symptoms of disease, or the predisposition toward disease. For example, "treatment" of a subject with no symptoms or clinically manifestations of a disease or disorder have been identified is preventive or prophylactic therapy. In one example, the lactic acid bacteria or probiotic bacterial sufficient to reduce or eliminate the microbial contamination in non-gut associated lymph nodes. Non-limiting examples of lymph nodes often found in different livestock include but are not limited to at least one of popliteal, intercostal, suprasternal, presternal, prepectoral, precrural, prescapular, ischiadic, prefemoral, sacral, sternal, cervical, renal, superficial inguinal, internal iliac, and external iliac, submaxillary, parotid, retropharyngeal, and lumbar lymph nodes, or equivalent thereof depending on the animal.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

As used herein, the terms "additive" and "feed additive" are used to describe compositions that may be used in conjunction with animal feed as feed additive resulting in an improvement of the health of livestock, poultry and fish, and a reduction or elimination of microbial contamination in non-gut associated lymph nodes. For example, the feed additive of the present invention may be used from bacterial isolates, partially or wholly degraded bacteria, isolated, isolated and purified from bacteria and/or synthesized synthetically in whole or in part. The additive or feed additive for the domestic animals, poultry and fishes may be of powder, grain or liquid form and will be used in accordance with the feeding condition and installations of the farm and the target animal.

Suitable animal feedstuffs include, e.g., green feed, silages, dried green feed, roots, tubers, fleshy fruits, grains and seeds, brewer's grains, pomace, brewer's yeast, distiller's spent grains, milling byproducts, byproducts of the production of sugar, starch and oil recovery and various food wastes. The feed additive of the present invention may be used alone or in conjunction with other well-known feed additives such as antioxidants or mixtures of various substances (mineral mixtures, vitamin mixtures) that can be added to such feeds for enhancement. Specific feeds may also be adapted for certain animal species depending on age and stages of development.

Base feeds suitable for use in conjunction with the peptides of the present invention may be prepared as is well-known to the artisan skilled in the art of preparing feeds, e.g., they may use those as described in Kirk-Othmer, Encyclopedia of Chemical Technology, 4th Ed., vol. 10, pp. 288-300, Wiley, N.Y., 1993, relevant portions incorporated herein by reference. For example, the base feed may include one or more of the following ingredients: corn, sorghum, barley, wheat, soybean, peanut, canola, fish meal, milk products, fats and oils, vitamins and minerals.

The present invention includes compositions and methods for the reduction or elimination of microbes, e.g., bacteria, from non-gut associated lymph node that enter the food chain as a result of animal meat that includes these lymph nodes. A lot of research has been conducted on treating the gut with probiotic bacteria that change the gut flora and that eliminates or crowds-out pathogenic bacteria. For example, U.S. Patent Application Publication No. 20040115177 shows the effect of probacteria in gut-associated lymph nodes, which are directly associated and are exposed to the gut flora.

However, the present inventors have found that the gut-associated lymphatic system, and bacteria associated therewith, e.g., in feces, differs significantly from the bacteria found in non-mesenteric (or gut-associated lymph nodes). The present inventors show in Gragg, et al., "Lymph Nodes, Feces, and Hides of Cattle at Slaughter" Applied and Environmental Microbiology, August 2013 Volume 79 Number 15 p. 4744-4750, when comparing lymph nodes from various parts of the animal (mandibular, mesenteric, mediastinal, subiliac, fecal, and hide), that different portions of the animal have very different exposure to bacteria. For example, *Salmonella* was isolated from 100% of the time in hide, with 94.1% in feces, and in mesenteric lymph nodes. The high percentage of *Salmonella* on the hide and in mesenteric or gut-associated lymph nodes is not surprising given the direct exposure of the surface of the hide and the gut-associated lymph nodes to the gut flora. A much smaller percentage of non-gut associated or non-mesenteric lymph nodes was identified, viz., 76.5% (subiliac), 55.9% (mandibular), and 7.4% (mediastinal). Furthermore, it was found that very different serotypes of typeable *Salmonella* were identified in the various lymph nodes. The inventors concluded that given the overrepresentation of some serotypes within certain lymph nodes, certain *Salmonella* strains may be better at entering the bovine host than other *Salmonella* strains or that some may be better adapted for survival within certain lymph nodes. As such, it was surprising and unexpected that a probiotic treatment would have a significant effect on non-gut associated lymph nodes.

Lactobacilli and other probiotic bacteria possessing the desired characteristics may be employed as a probiotic in the present invention. Typically, however, the bacteria are selected from among the genera *Lactobacillus, Lactococcus, Leuconostoc, Pediococcus, Enterococcus* and *Streptococcus*. In one embodiment the LAB employed as a probiotic is from the genera *Lactobacillus*. In yet another embodiment, the strain of *Lactobacillus* is selected from *L. acidophilus, L. bulgaricus, L. helveticus, L. casei, L. lactis, L. plantarum, L. rhamnosus, L. reuteri, L. fermentum, L. brevis, L. delbreukii, L. cellobiosus,* and *L. salivarius*.

Probiotic bacteria (such as a specific strain of Lactobacilli, NP51 combined with a *Propionibacterium*, PF24) are currently fed to cattle to improve animal performance. We have recently completed studies that have demonstrated that the use of probiotic bacteria can reduce the presence and concentration of *Salmonella* in the lymph nodes of cattle at harvest. Our concept is that lactic acid and other probiotic bacteria can reduce pathogens in the lymph nodes and other lymphatic tissues of cattle and other livestock.

Cattle are fed commercial feed rations supplemented with probiotic bacteria such as NP51 combined with the PF24. The product is administered daily in the feed for the duration of time the animal is in the feed yard and has been proven to reduce the prevalence and concentration of *Salmonella* in the lymph nodes. However, it is possible that shorter feeding periods will yield similar results. Additionally, this product could also be used in dairy cattle and swine to reduce the presence of *Salmonella* in the lymph nodes and other lymphatic tissues. Finally, it is possible that other combinations of lactic acid bacteria and other probiotic bacteria can also reduce the presence of pathogens in livestock.

This invention reduces the prevalence and concentration of *Salmonella* in the lymph nodes of livestock thus ultimately reducing the risk to public health due to *Salmonella* in, e.g., beef, pigs, goats, or sheep. Other pathogens can also be controlled in the lymph nodes or in other lymphatic tissues that are not associated with the gut.

Direct-Fed Microbials as an Aid in the Control of Foodborne Pathogens in Cattle Lymph Nodes and Fecal Samples.

The goal of this project was to determine pathogen reductions in cattle as a result of feeding a direct-fed microbial. The objectives were: 1) Determine if supplementing diets with a high dose ($10^9$/animal/day) of *Lactobacillus acidophilus* NP51 (HNP51) will reduce *Salmonella* in lymph nodes at slaughter; and 2) Determine reductions in fecal pathogens for cattle supplemented with HNP51.

Commercial and research feedlot studies. The treatments for both studies were controls (i.e., not fed HNP51) and animals whose diets were supplemented with $10^9$/head/day HNP51. In the commercial study, approximately 1,800 cattle were randomized into two treatments with 12 pens/treatment and 75 head/pen. Twenty-five fecal pats were taken from each pen (n=600). Subiliac lymph nodes (LN) were obtained from approximately 25 animals/pen (n=600) at the slaughter facility. In the research feedlot study, 112 cattle were randomized to 14 pens/treatment and 4 head/pen. Fecal grab samples were collected prior to shipment to a commercial slaughter facility where subiliac lymph nodes (LN) were also collected. For both studies, LN were assayed for *Salmonella* using both qualitative and quantitative methods. Fecal samples were assayed for *Salmonella, E. coli* O157, and the genes that encode the 'Big 6' non-O157 serogroup antigens. In addition, quantitative estimates were derived for fecal samples that were positive for *E. coli* O157.

Figure 1B:
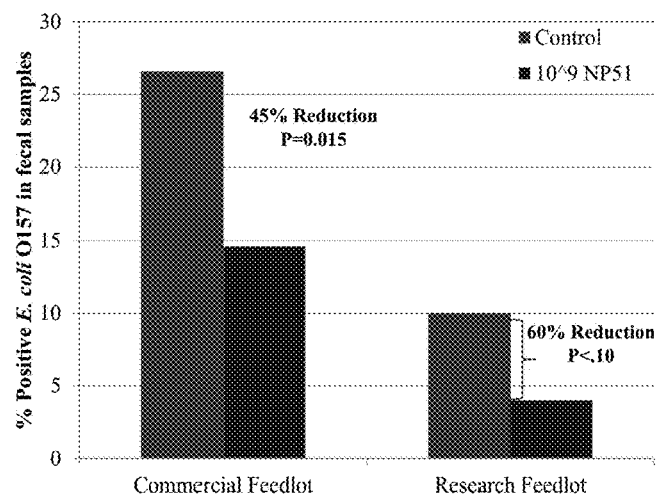
Figure 2A:
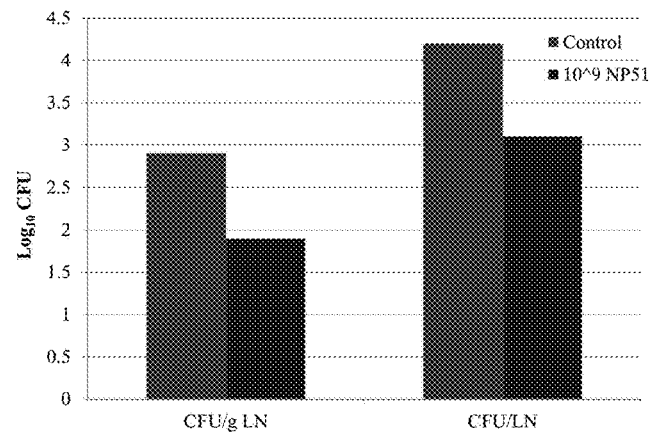
FIGS. 2A and 2B show the concentration of *Salmonella* in lymph nodes (FIG. 2A) and the concentration shift of *Salmonella* (FIG. 2B) in cattle fed HNP51 in a commercial feedlot. 0: positive but below limit of concentration & le 1 log 10 cfu/g; 1: >1 log 10 cfu/g & le 2 log 10 cfu/g; 2: >2 log 10 cfu/g & le 3 log 10 cfu/g; 3: >3 log 10 cfu/g & le 4 log 10 cfu/g; 4: >4 log 10 cfu/g & le 5 log 10 cfu/g; and 5: >5 log 10 cfu/g.
Figure 2B:
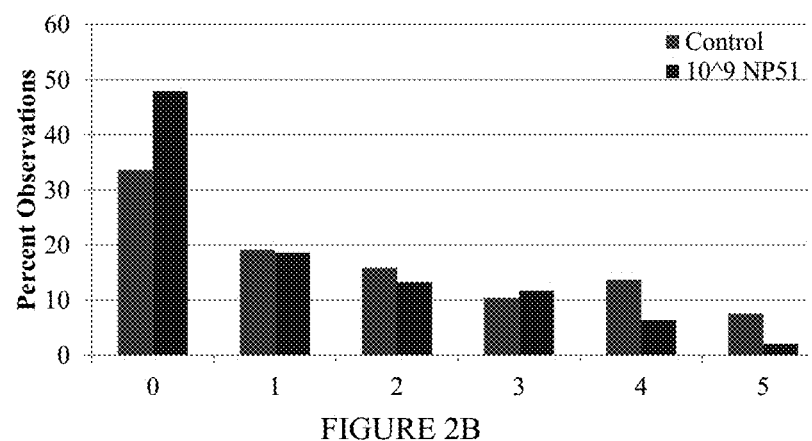

Lymph nodes—For the commercial and research feedlot studies, *Salmonella* was recovered from 25% (p<0.01) and 88% (p<0.05) fewer lymph nodes, respectively, for cattle fed HNP51 (FIGS. 1A and 1B). The concentration of *Salmonella* on a CFU/g LN and CFU/LN basis was also less for animals given HNP51 in the commercial feedlot (FIGS. 2A and 2B).

Fecal samples—A 45% (p=0.02) and 60% (p=0.10) reduction in *E. coli* O157 prevalence was observed among cattle administered HNP51 in both feedlot studies, respectively (FIG. 1). Fewer fecal samples collected in the commercial feedlot from animals administered HNP51 were positive for the genes that encode non-O157 serogroups O26 (53% reduction relative to control; p=0.02), O45 (41%; p=0.02), O103 (35%; p=0.03), and O121 (47%; p=0.02). No differences were observed in the research feedlot study. In both studies, cattle administered HNP51 had a lower numerical—but not statistically significant—prevalence of *Salmonella* relative to the control cattle.

The results of both the commercial and research feedlot studies indicate that the pre-harvest administration of the direct-fed microbial, HNP51, is an effective tool that aids in the control of *Salmonella* within lymph nodes and various pathogens in the feces of feedlot cattle. Reducing the carriage of *Salmonella* in the lymph nodes of cattle will result in decreased contamination of ground beef from the lymph nodes and associated tissue included in this product. Decreased fecal pathogens will potentially result in more effective post-harvest interventions due to the reduced pathogen loads entering the processing plants. All of the pathogen reductions will serve to reduce outbreaks/product recalls and to protect public health.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Sara E. Gragg, Guy H. Loneragan, Kendra K. Nightingale, Oayna M. Brichta-Harhay, Henry Ruiz, Jacob R. Elder, Lyda G. Garcia, Markus F. Miller, Alejandro Echeverry, Rosa G. Ramirez Porras, Mindy M. Brashears, "Lymph Nodes, Feces, and Hides of Cattle at Slaughter" Applied and Environmental Microbiology, August 2013 Volume 79 Number 15 p. 4744-4750.

United States Patent Application No. 20040115177.

What is claimed is:

1. A method of eliminating or reducing pathogenic bacterial contamination in lymph nodes that enter the food supply from livestock comprising:
    identifying an animal in need of eliminating or reducing pathogenic bacterial contamination in popliteal, intercostal, suprasternal, presternal, prepectoral, precrural, prescapular, ischiadic, prefemoral, sacral, sternal, cervical, renal, superficial inguinal, internal iliac, external iliac, submaxillary, parotid, retropharyngeal, or lumbar lymph nodes that enter the food supply; and
    providing the animal with an effective amount of a lactic acid bacteria or probiotic bacteria sufficient to reduce or eliminate the pathogenic bacterial contamination in the lymph nodes.

2. The method of claim 1, wherein the lactic acid bacteria is Lactobacilli NP51.

3. The method of claim 1, wherein the probiotic bacteria is *Propionibacterium* PF24.

4. The method of claim 1, wherein the lactic acid bacteria is Lactobacilli, NP51, and is combined with the probiotic bacteria *Propionibacterium*, PF24.

5. The method of claim 1, wherein the lymph nodes are treated with the lactic acid bacteria or probiotic bacteria to eliminate the microbial contamination prior to entering the food supply.

6. The method of claim 1, wherein the animal is selected from cattle, pigs, sheep, goats, bison, rabbit, turkey, goose, duck, or chicken.

7. The method of claim 1, wherein the pathogenic bacteria that infect lymph nodes are selected from at least one of food-borne human and animal bacterial pathogens.

8. The method of claim 1, wherein the pathogenic bacteria that infect lymph nodes are selected from at least one of *Salmonella*, pathogenic *E. coli*, *Campylobacter*, or *Listeria monocytogenes*.

9. A method of eliminating or reducing pathogenic bacterial contamination in lymph nodes that enter the food supply from livestock comprising:
    identifying an animal in need of eliminating or reducing pathogenic bacterial contamination in popliteal, intercostal, suprasternal, presternal, prepectoral, precrural, prescapular, ischiadic, prefemoral, sacral, sternal, cervical, renal, superficial inguinal, internal iliac, external iliac, submaxillary, parotid, retropharyngeal, or lumbar lymph nodes that enter the food supply; and
    providing the animal with an effective amount or a lactic acid bacteria or probiotic bacteria sufficient to reduce or eliminate the pathogenic bacterial contamination the in lymph nodes.

10. The method of claim 9, wherein the lactic acid bacteria is Lactobacilli NP51.

11. The method of claim 9, wherein the probiotic bacteria is *Propionibacterium* PF24.

12. The method of claim 9, wherein the lactic acid bacteria is Lactobacilli, NP51, and is combined with the probiotic bacteria *Propionibacterium*, PF24.

13. The method of claim 9, wherein the lymph nodes are treated with the lactic acid bacteria or probiotic bacteria to eliminate the microbial contamination prior to entering the food supply.

14. The method of claim 9, wherein the lymph nodes are non-mesenteric.

15. The method of claim 9, wherein the animal is selected from cattle, pigs, sheep, goats, bison, rabbit, turkey, goose, duck, or chicken.

16. The method of claim 9, wherein the pathogenic bacteria that infect the lymph nodes are selected from at least one of food-borne human and animal bacterial pathogens.

17. The method of claim 9, wherein the pathogenic bacteria that infect the lymph nodes are selected from at least one of *Salmonella*, pathogenic *E. coli*, *Campylobacter*, or *Listeria monocytogenes*.

* * * * *